United States Patent
Sato et al.

(10) Patent No.: US 10,548,464 B2
(45) Date of Patent: Feb. 4, 2020

(54) ENDOSCOPE

(71) Applicant: OLYMPUS CORPORATION, Tokyo (JP)

(72) Inventors: Eijiro Sato, Hachioji (JP); Chikayoshi Meguro, Hachioji (JP); Kenji Takatsuji, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 256 days.

(21) Appl. No.: 15/687,597

(22) Filed: Aug. 28, 2017

(65) Prior Publication Data

US 2017/0354319 A1 Dec. 14, 2017

Related U.S. Application Data

(63) Continuation of application No. PCT/JP2016/079064, filed on Sep. 30, 2016.

(30) Foreign Application Priority Data

Dec. 17, 2015 (JP) ................ 2015-246017

(51) Int. Cl.
*A61B 1/00* (2006.01)
*A61B 1/005* (2006.01)
*A61B 1/018* (2006.01)

(52) U.S. Cl.
CPC .......... *A61B 1/0052* (2013.01); *A61B 1/0057* (2013.01); *A61B 1/018* (2013.01)

(58) Field of Classification Search
CPC ..... A61B 1/0052; A61B 1/0057; A61B 1/018; A61B 1/00121; A61B 1/00066; A61B 1/00039; A61B 1/00105; G02B 23/24
See application file for complete search history.

(56) References Cited

U.S. PATENT DOCUMENTS 5,785,644 A * 7/1998 Grabover ........... A61B 1/00052
600/109
6,004,264 A 12/1999 Sano et al.
(Continued)

FOREIGN PATENT DOCUMENTS

JP H03-289931 A 12/1991
JP H08-010220 A 1/1996
(Continued)

OTHER PUBLICATIONS

International Search Report dated Nov. 8, 2016 issued in PCT/JP2016/079064.
(Continued)

*Primary Examiner* — Timothy J Neal
(74) *Attorney, Agent, or Firm* — Scully, Scott, Murphy & Presser, P.C.

(57) ABSTRACT

In an endoscope including a rear grasping portion extending along a second longitudinal axis that is a direction flexed relative to a first longitudinal axis along which the operation portion body extends, a bend preventing portion covering a universal cable extending out from the proximal end side of the rear grasping portion is joined to the proximal end side of the rear grasping portion via a movable joint portion so that a direction of the bend preventing portion can be changed by the movable joint portion to a first direction oriented to the inner side in the flexion direction of the rear grasping portion relative to the operation portion body and a second direction oriented to the outer side in the flexion direction of the rear grasping portion relative to operation portion body.

7 Claims, 12 Drawing Sheets

(56) References Cited

U.S. PATENT DOCUMENTS

| | | | | |
|---|---|---|---|---|
| 6,520,908 | B1 * | 2/2003 | Ikeda | A61B 1/00066 600/110 |
| 10,206,559 | B2 * | 2/2019 | Sato | A61B 1/00114 |
| 2007/0276183 | A1 | 11/2007 | Melder | |
| 2010/0160729 | A1 * | 6/2010 | Smith | A61B 1/00098 600/114 |
| 2011/0295068 | A1 | 12/2011 | Petersen et al. | |
| 2012/0165605 | A1 * | 6/2012 | Yamazaki | A61B 1/00066 600/106 |
| 2016/0242629 | A1 | 8/2016 | Hijihara et al. | |

FOREIGN PATENT DOCUMENTS

| | | |
|---|---|---|
| JP | H11-146878 A | 6/1999 |
| JP | 2001-095747 A | 4/2001 |
| JP | 2005-027901 A | 2/2005 |
| JP | 2008-545449 A | 12/2008 |
| JP | 2009-189684 A | 8/2009 |
| JP | 2012-511356 A | 5/2012 |
| WO | 2015/141039 A1 | 9/2015 |

OTHER PUBLICATIONS

Extended Supplementary European Search Report dated Sep. 12, 2018 in European Patent Application No. 16 87 5210.3.

* cited by examiner

ENDOSCOPE

CROSS REFERENCE TO RELATED APPLICATION

This application is a continuation application of PCT/JP2016/079064 filed on Sep. 30, 2016 and claims benefit of Japanese Application No. 2015-246017 filed in Japan on Dec. 17, 2015, the entire contents of which are incorporated herein by this reference.

BACKGROUND OF THE INVENTION

1. Field of the Invention

The present invention relates to an endoscope including an operation portion allowing a plurality of grasping modes.

2. Description of the Related Art

Conventionally, endoscopes are used to perform observation of a target region inside a subject such as a body cavity and, as necessary, various kinds of treatment using a treatment instrument inserted in a treatment instrument channel, by inserting an elongated insertion portion into the subject.

As this type of endoscope, a flexible endoscope in which a distal end portion, a bending portion and a flexible tube portion are arranged in this order from a distal end side has been widely used. When the insertion portion of such a flexible endoscope is inserted into a subject, a surgeon or the like grasps the flexible tube portion with one of his/her hands and pushes the insertion portion into the subject while grasping the operation portion with the other of his/her hands. In this case, the surgeon or the like can bend the bending portion in a desired direction by operating an operation knob arranged at the operation portion with the hand grasping the operation portion.

For example, when endoscopic observation or treatment of, e.g., a urinary organ or a nasal cavity is performed, the insertion portion is inserted substantially horizontally to a subject such as a recumbent patient. In order to enhance such insertability to a target region, for example, Japanese Patent Application Laid-Open Publication No. 2009-189684 discloses an operation portion (operation/grasping portion) having a substantial L shape in which a grasping portion provided in the operation portion extends from the proximal end side of an operation portion body (operation portion) so as to be inclined at a predetermined angle relative to a direction in which the operation portion body extends. Also, in the technique in Japanese Patent Application Laid-Open Publication No. 2009-189684, at a proximal end of the grasping portion, a bend preventing portion extending along a direction in which the grasping portion extends is provided, and one end side of a universal cable of the bend preventing portion is protected by the bend preventing portion.

SUMMARY OF THE INVENTION

An endoscope according to an aspect of the present invention includes: an operation portion body provided so as to be continuous with a proximal end side of an insertion portion; a rear grasping portion provided so as to be continuous with a proximal end side of the operation portion body, the rear grasping portion extending along a second longitudinal axis that is a flexion direction flexed relative to a first longitudinal axis along which the operation portion body extends; a cable portion extending out from a proximal end side of the rear grasping portion; a tube portion covering the cable portion on the proximal end side of the rear grasping portion; and a movable joint portion configured to join the tube portion to the proximal end side of the rear grasping portion, the movable joint portion being pivotable around a pivot axis inclined to an outer side in the flexion direction relative to the second longitudinal axis so that a direction of the tube portion can be changed.

DETAILED DESCRIPTION OF THE PREFERRED EMBODIMENT(S)

Figure 1:
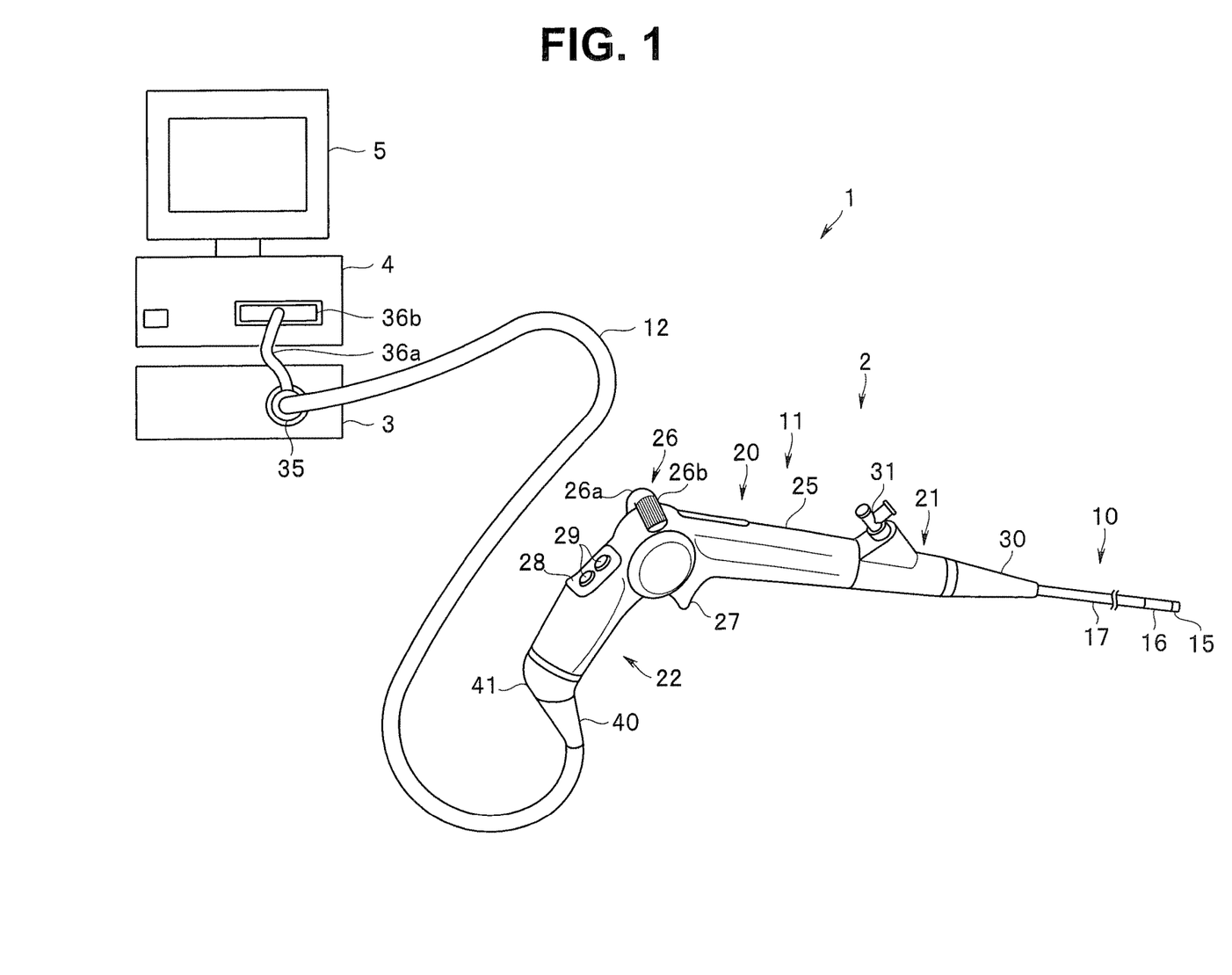
FIG. 1 is a schematic configuration diagram of an endoscope system.
Figure 2:
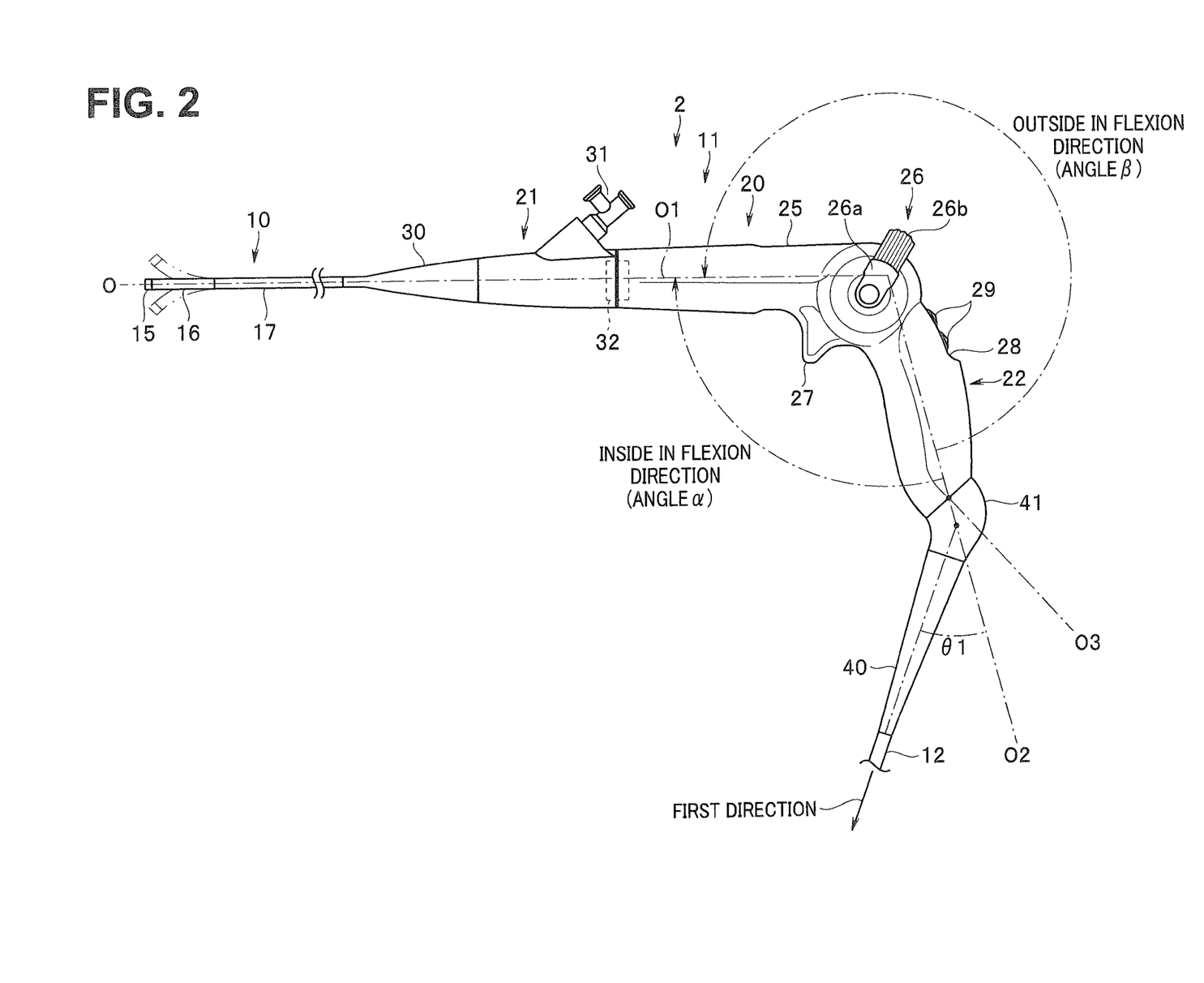
FIG. 2 is a side view of an endoscope, a universal cable of which is oriented in a first direction.
Figure 3:
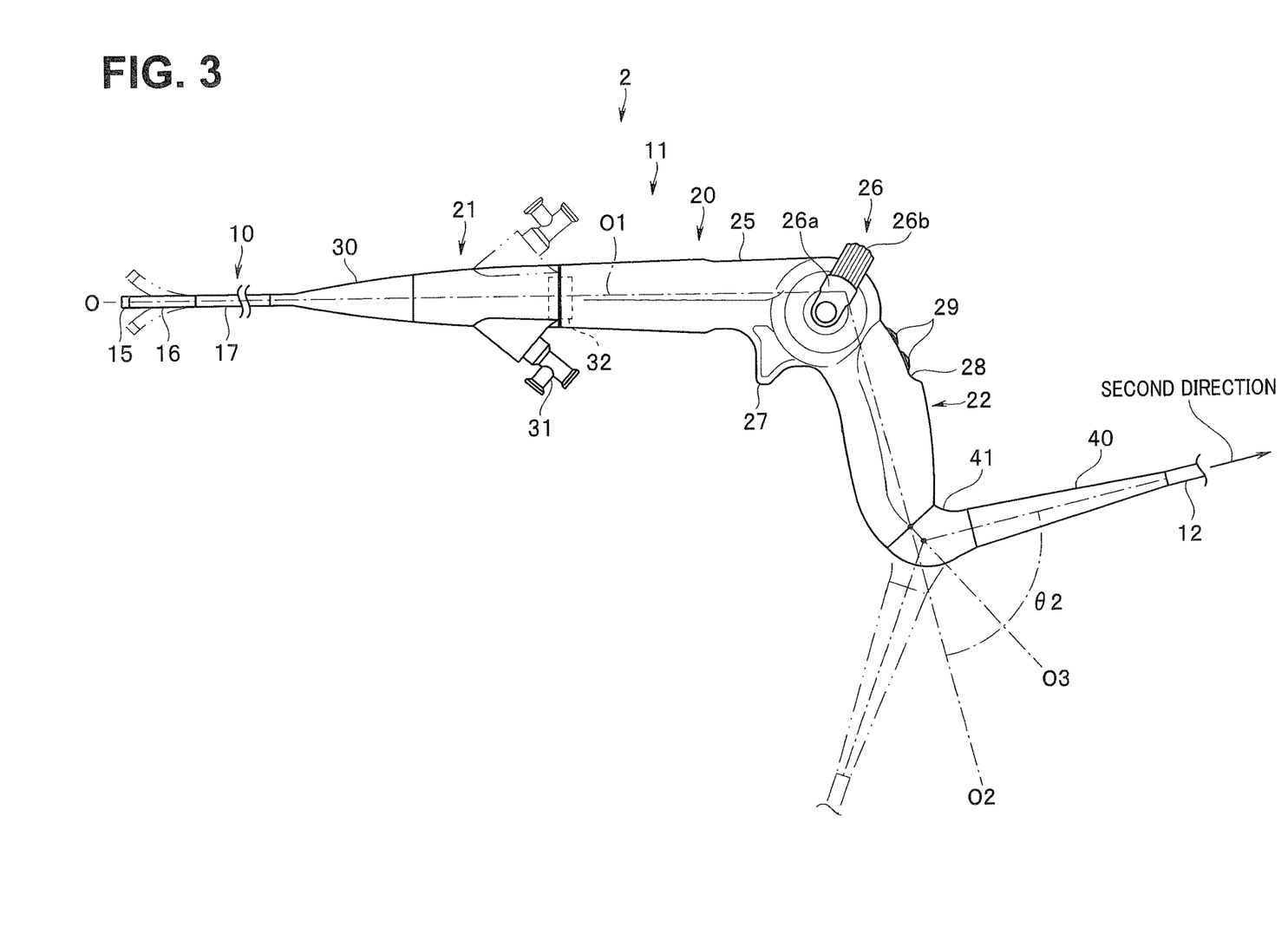
FIG. 3 is a side view of the endoscope, the universal cable of which is oriented in a second direction.
Figure 4:
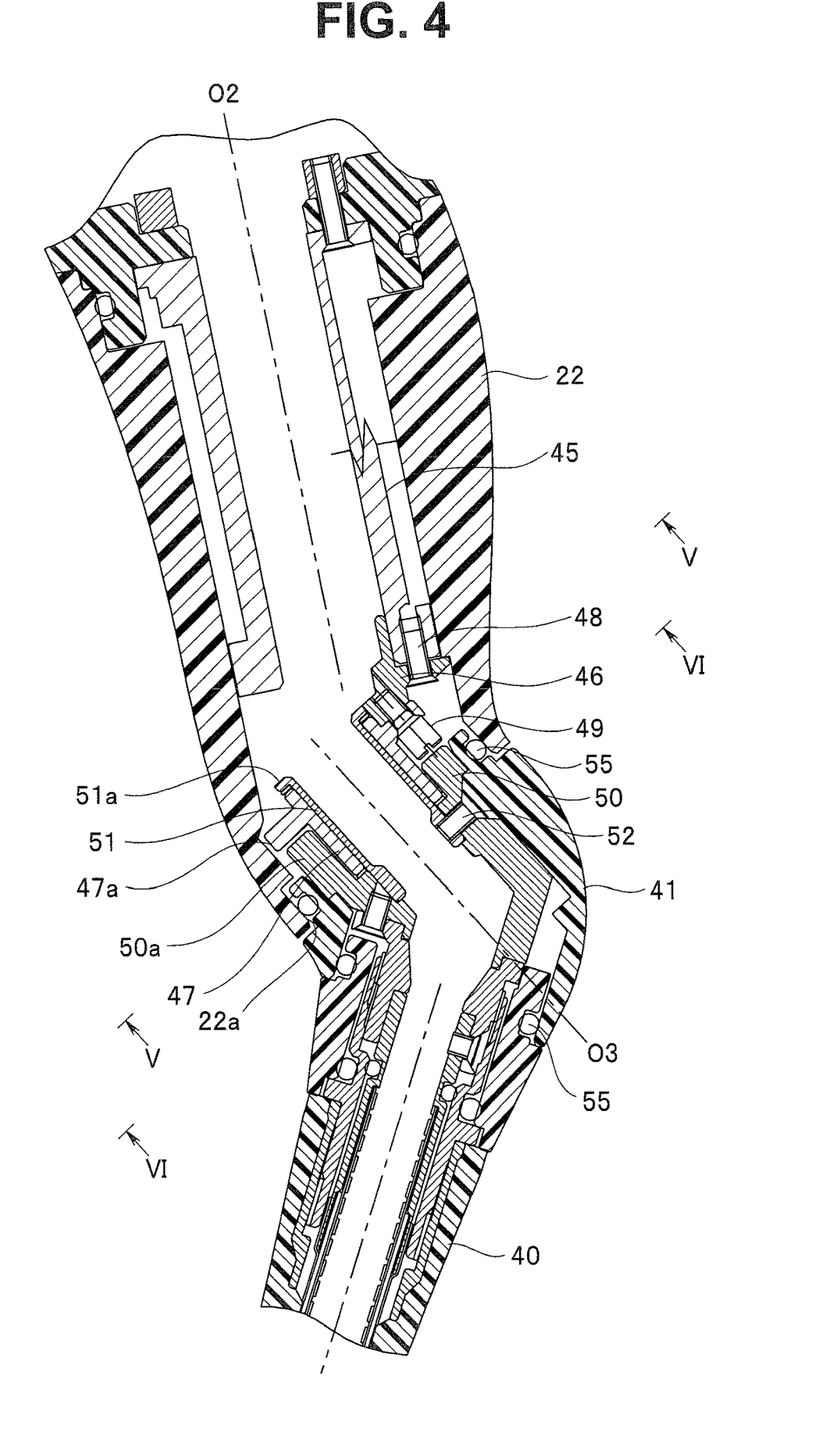
FIG. 4 is a major part cross-sectional view illustrating an inner structure of a rear grasping portion.
Figure 5:
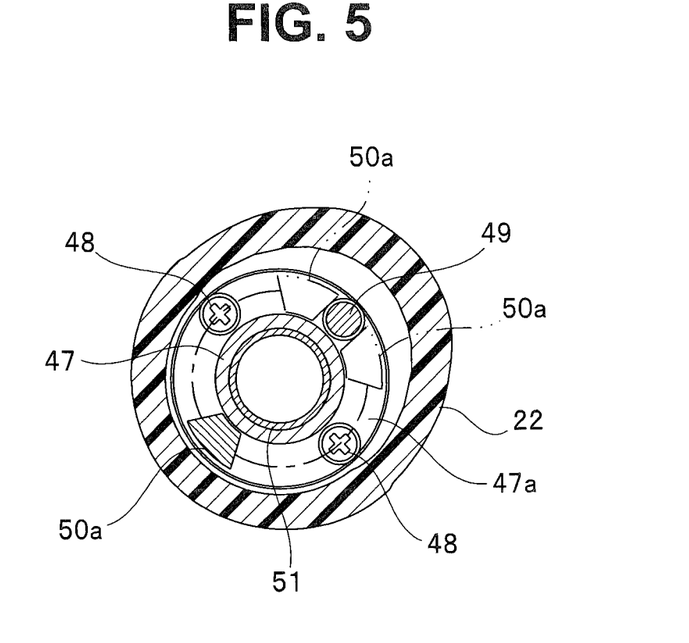
FIG. 5 is a cross-sectional view along line V-V in FIG. 4.
Figure 6:
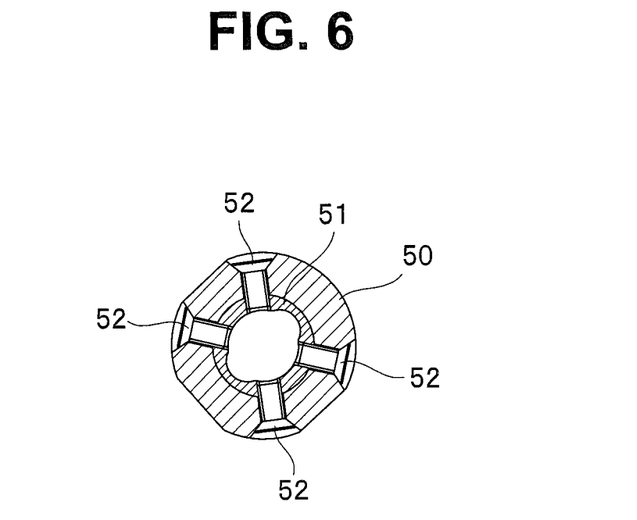
FIG. 6 is a cross-sectional view along line VI-VI in FIG. 4.
Figure 7:
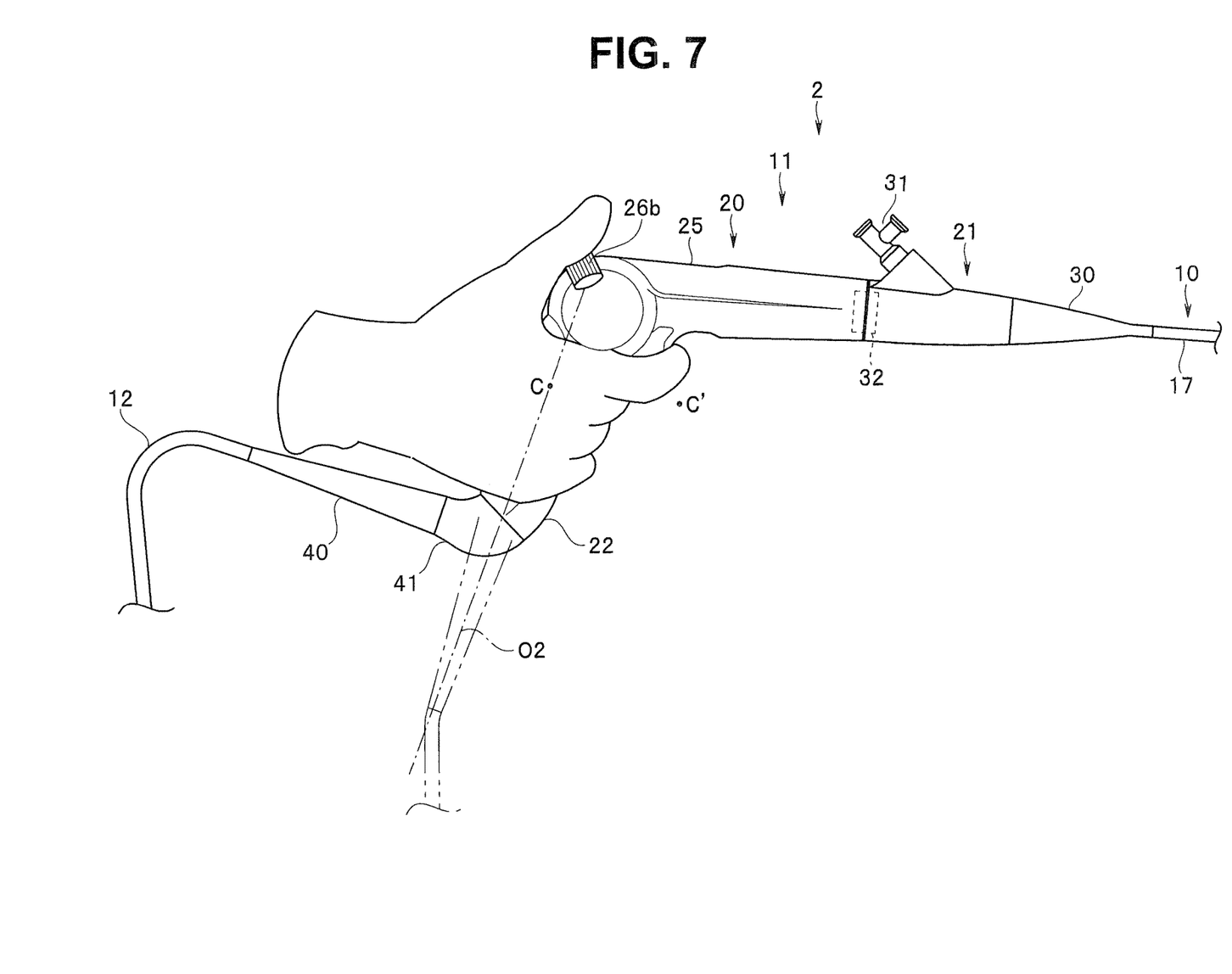
FIG. 7 is a diagram illustrating a favorable example of grasping when a rear grasping portion is grasped.
Figure 8:
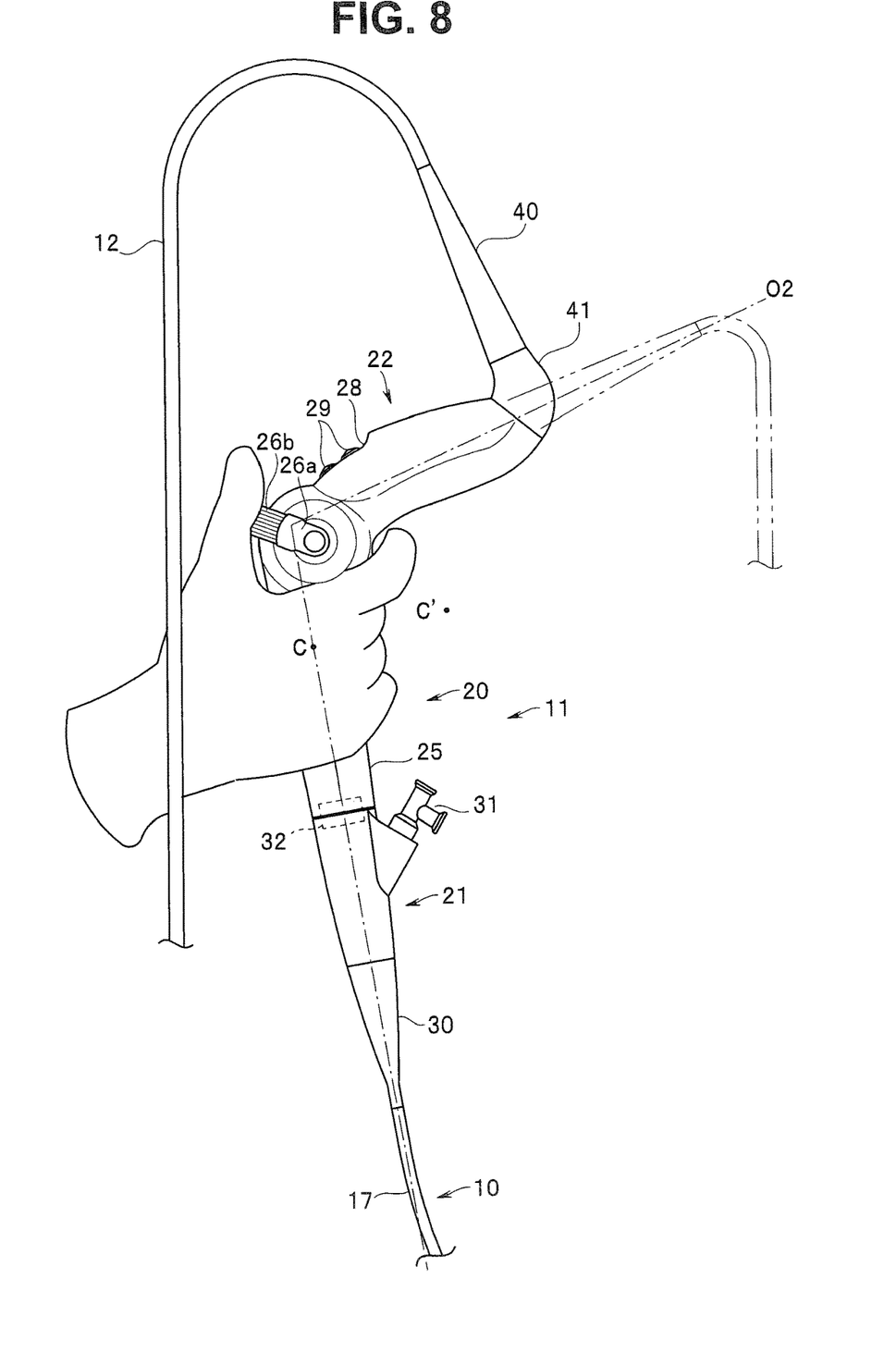
FIG. 8 is a diagram illustrating a favorable example of grasping when a front grasping portion is grasped.
Figure 9:
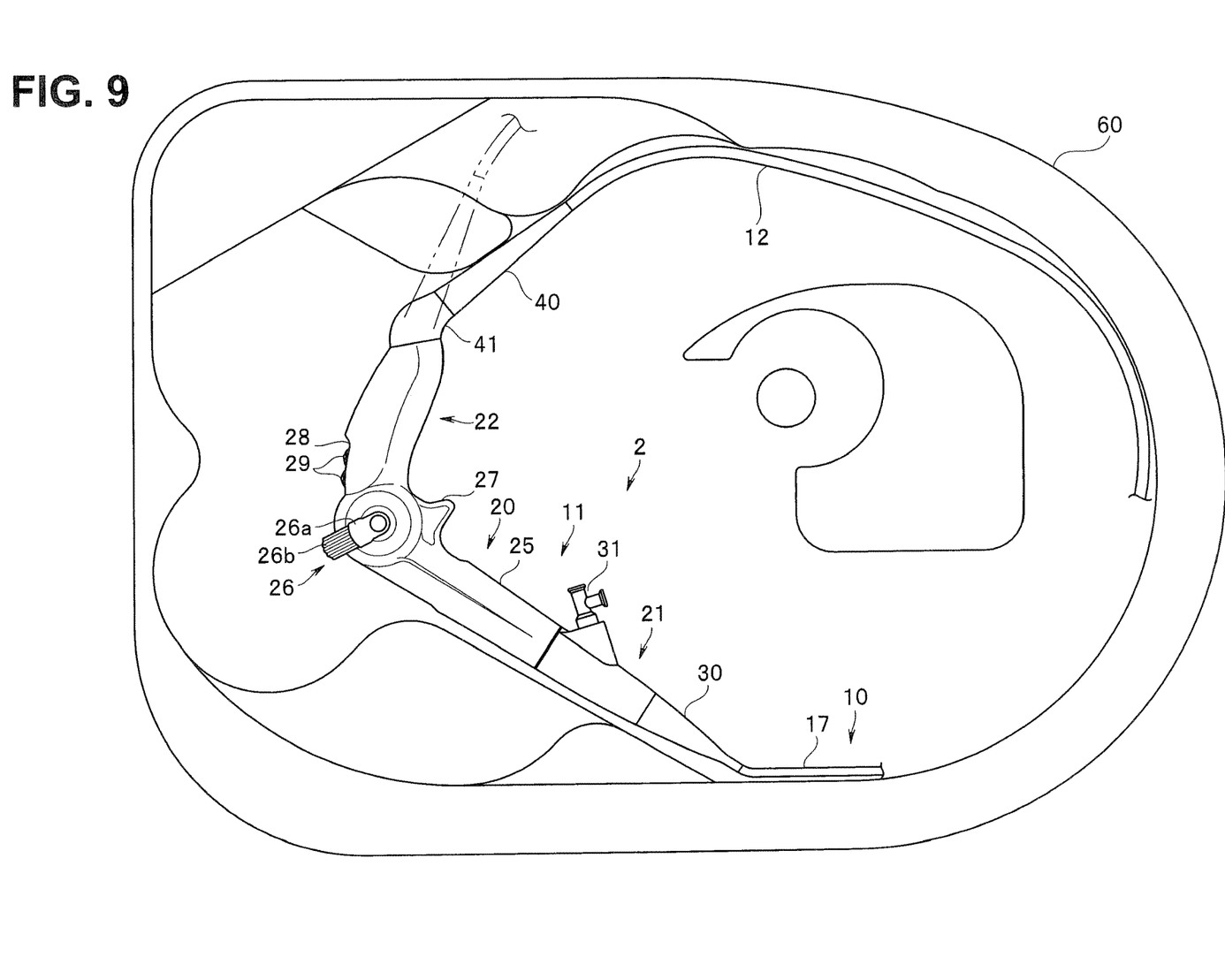
FIG. 9 is a diagram illustrating a state in which an endoscope is stored in a cleaning basin of a cleaning apparatus.

A mode of the present invention will be described below with reference to the drawings. The drawings relate to an embodiment of the present invention: FIG. 1 is a schematic configuration diagram of an endoscope system; FIG. 2 is a side view of an endoscope, a universal cable of which is oriented in a first direction; FIG. 3 is a side view of the endoscope, the universal cable of which is oriented in a second direction; FIG. 4 is a major part cross-sectional view illustrating an inner structure of a rear grasping portion; FIG. 5 is a cross-sectional view along line V-V in FIG. 4; FIG. 6 is a cross-sectional view along line VI-VI in FIG. 4; FIG. 7 is a diagram illustrating a favorable example of grasping when a rear grasping portion is grasped; FIG. 8 is a diagram illustrating a favorable example of grasping when a front grasping portion is grasped; and FIG. 9 is a diagram illustrating a state in which an endoscope is stored in a cleaning basin of a cleaning apparatus.

An endoscope system 1, which is illustrated in FIG. 1, includes an endoscope 2, a light source apparatus 3 configured to supply illuminating light to the endoscope 2, a video processor 4 including a camera control unit (CCU) configured to perform image processing on a video signal obtained as a result of image pickup by the endoscope 2, and a monitor 5 configured to display the video signal outputted from the video processor 4.

The endoscope 2 according to the present embodiment illustrated in FIGS. 1 to 3 is, for example, a urological endoscope. This endoscope 2 includes a long insertion portion 10 that can be inserted into a target region inside a subject, an operation portion 11 provided so as to be continuous with the proximal end side of the insertion portion 10, and a universal cable 12, which is a cable portion extending out from the operation portion 11.

A major part of the insertion portion 10 includes a rigid distal end portion 15, a bending portion 16 and a flexible tube portion 17 having flexibility, which are provided in this order from the distal end side.

In the distal end portion 15, an image pickup unit incorporating an image pickup device such as a CCD or a CMOS is held, and a signal wire inserted in the insertion portion 10 is electrically connected to the image pickup unit. Also, in the distal end portion 15, an illuminating optical system is held, and a light guide bundle inserted in the insertion portion 10 is optically connected to the illuminating optical system. Also, in the distal end portion 15, a treatment instrument channel port is provided, and a treatment instrument channel inserted in the insertion portion 10 communicates with the treatment instrument channel port (none of these components illustrated).

The bending portion 16 is bendable, for example, only in two directions, up and down, according to a bending operation performed via the operation portion 11. Note that the bending portion 16 may be configured to be bendable in four directions, up/down and left/right.

The flexible tube portion 17 includes a flexible tubular member that can be bent passively.

As illustrated in FIGS. 2 and 3, the operation portion 11 includes an operation portion body 20 provided so as to be continuous with the proximal end side of the insertion portion 10, a distal end rotating portion 21 interposed between the insertion portion 10 and the operation portion body 20, and a rear grasping portion 22 provided so as to be continuous with the proximal end side of the operation portion body 20.

The operation portion body 20 includes, for example, a substantially elliptic cylindrical member, and extends along a first longitudinal axis O1 set coaxially with an insertion axis O of the insertion portion 10.

In a distal end-side area of the operation portion body 20, a front grasping portion 25, which is a first grasping portion for, e.g., a surgeon to grasp the operation portion 11 along the insertion axis O direction, is set.

Also, on the proximal end side of the operation portion body 20, a bending operation lever 26 for performing an operation to bend the bending portion 16 is provided. The bending operation lever 26 has, for example, a cantilevered L shape resulting from a lever portion 26a and a finger rest portion 26b, which is provided on the free end side of the lever portion 26a, being integrally formed, and the fixed end side of the lever portion 26a is pivotally supported by a side portion of the operation portion body 20. The bending operation lever 26 is joined to a well-known wire pulling mechanism (not illustrated) provided in the operation portion body 20. Consequently, upon the bending operation lever 26 being operated so as to pivot, wires inserted in the insertion portion 10 are pulled or loosened, which causes the bending portion 16 to bend.

Furthermore, on the proximal end side of the operation portion body 20, a projecting-shape finger hook portion 27 is provided at a region on the opposite side of the finger rest portion 26b across the operation portion body 20.

The distal end side of the distal end rotating portion 21 is continuous with the proximal end side of the insertion portion 10 via the bend preventing portion 30.

Also, at a side portion of the distal end rotating portion 21, a treatment instrument insertion port 31 is provided so as to project, and the treatment instrument insertion port 31 communicates with the treatment instrument channel inside the distal end rotating portion 21.

Furthermore, the proximal end side of the distal end rotating portion 21 is pivotally joined to the distal end side of the operation portion body 20 via a rotation mechanism 32. Here, the rotation mechanism 32 in the present embodiment is capable of, for example, pivoting the distal end rotating portion 21 around the first longitudinal axis O1 of the operation portion body 20 within a pivot range of 180°. Pivoting of the distal end rotating portion 21 causes the treatment instrument insertion port 31 to be pivoted integrally with the insertion portion 10 and thus enables the treatment instrument insertion port 31 to be moved to an optimum position according to a state of grasping of the operation portion 11 (see FIGS. 2 and 3). Here, the pivot range of the rotation mechanism 32 is not limited to 180°, and can be set, for example, as an arbitrary angular range of no more than 360°.

The rear grasping portion 22 includes, for example, a substantially elliptic cylindrical shape, and extends along a second longitudinal axis O2, which is a direction flexed relative to the first longitudinal axis O1.

In the present embodiment, the rear grasping portion 22 is disposed in a flexed manner on the proximal end side of the operation portion body 20 so that an angle α on the minor angle side of the second longitudinal axis O2 relative to the first longitudinal axis O1 is, for example, an obtuse angle of 105°. Consequently, the rear grasping portion 22 functions as a second grasping portion that enables the operation portion 11 to be grasped in a direction that is different from the direction of grasping of the front grasping portion 25.

In this case, in order to achieve a same level of operability in bending operation regardless of whether the front grasping portion 25 or the rear grasping portion 22 is grasped, the bending operation lever 26 projects on the outer side in the direction of flexion between the operation portion body 20 and the rear grasping portion 22 so that when the bending operation lever 26 is in a neutral state in which no bending operation is performed, the finger rest portion 26b is positioned at a rough center of an angle β formed between the first longitudinal axis O1 and the second longitudinal axis O2 on the major angle side. On the other hand, the finger hook portion 27 is disposed on the inner side in the direction of flexion between the operation portion body 20 and the rear grasping portion 22 so as to project at a rough center of the angle α between the first longitudinal axis O1 and the second longitudinal axis O2 on the minor angle side.

Also, in the vicinity of the bending operation lever 26, a recess portion 28 is provided in a back face of the rear grasping portion 22, and in the recess portion 28, switches 29 for various kinds of endoscope functions are provided.

The universal cable 12 is a composite cable that allows insertion of, e.g., various signal wires and a light guide extending from the distal end side of the insertion portion 10 to the operation portion 11 through the inside of the insertion portion 10 and further extending out from the operation portion 11. Also, the universal cable 12 may allow insertion of, e.g., an air/water feeding tube extending out from an air/water feeding apparatus (not illustrated).

The universal cable 12 extends out from the proximal end side of the rear grasping portion 22. Also, at an extension end of the universal cable 12, an endoscope connector 35 that is connectable to the light source apparatus 3 is provided. Furthermore, a signal cable 36a extends out from a side face portion of the endoscope connector 35, and at an extension end of the signal cable 36a, an electric connector portion 36b that is connectable to the video processor 4 is provided.

Here, on the proximal end side of the rear grasping portion 22, a bend preventing portion 40 is provided as a tube portion covering the universal cable 12. In the present embodiment, the bend preventing portion 40 is intended to gradually change a stiffness of an area covering the universal cable 12 to prevent, e.g., buckling on the rear grasping portion 22 side of the universal cable 12. Thus, the bend preventing portion 40 is set so as to have a stiffness that is high on the rear grasping portion 22 side (that is, rigid) and is lower (that is, is more flexible) toward the extension end side from which the universal cable 12 is exposed.

The bend preventing portion 40 is joined to the proximal end side of the rear grasping portion 22 via a movable joint portion 41. Then, the interposition of the movable joint portion 41 enables a direction of the bend preventing portion 40 to be changed to a first direction oriented to the inner side in the flexion direction of the rear grasping portion 22 relative to the operation portion body 20 (see FIG. 2) and a second direction oriented to the outer side in the flexion direction of the rear grasping portion 22 relative to the operation portion body 20 (see FIG. 3).

In this case, it is desirable that the first direction be, for example, inclined to the inner side in the flexion direction relative to the direction of the second longitudinal axis O2 of the rear grasping portion 22 within a range of 20 to 40 degrees, and in the present embodiment, an angle θ1 of the inclination of the first direction relative to the second longitudinal axis O2 is set at approximately 35 degrees.

Also, it is desirable that the second direction be, for example, inclined to the outer side in the flexion direction relative to the direction of the second longitudinal axis O2 of the rear grasping portion 22 at an angle of no less than 80 degrees, and in the present embodiment, an angle θ2 of the inclination of the second direction relative to the second longitudinal axis O2 is set at approximately 90 degrees. Consequently, the second direction in the present embodiment is set in, for example, a direction that is substantially parallel to the first longitudinal axis O1 within an error range of around ±15 degrees.

Next, a structure of joining of the movable joint portion 41 to the rear grasping portion 22 will be described in detail.

As illustrated in FIG. 4, inside the rear grasping portion 22, a guide barrel 45 for allowing insertion of cables and the like such as various signals wires, the light guide and the air/water feeding tube that extend out from the operation portion body 20 side is provided fixedly.

Also, on the proximal end side of the rear grasping portion 22, an opening portion 22a is provided, and a bracket 46 fixedly provided on the proximal end side of the guide barrel 45 is faced to the opening portion 22a.

Also, in the opening portion 22a, a substantially cylindrical shaft member 47 is arranged. An outward flange 47a is provided at an outer circumferential portion of the shaft member 47, and the outward flange 47a is fastened to the bracket 46 with screws 48 (see FIG. 5), and the shaft member 47 is thus held in the rear grasping portion 22.

On the other hand, inside the movable joint portion 41, an outer barrel member 50 fitted on the outer circumferential side of the shaft member 47 is provided. Also, an inner barrel member 51 is fitted in the inner circumferential side of the shaft member 47. At an end portion of the inner barrel member 51, an engagement portion 51a that is engageable with an end face of the shaft member is provided, and the inner barrel member 51 is fastened to the outer barrel member 50 with screws 52 (see FIG. 6). Consequently, the movable joint portion 41 is joined to the rear grasping portion 22 so as to be pivotable with a center axis of the shaft member 47 as a pivot axis O3.

In this case, in order to make the inclination angle θ2 of the second direction larger than the inclination angle θ1 of the first direction, the pivot axis O3 is set so as to be inclined to the outer side in the flexion direction relative to the second longitudinal axis O2.

Also, in order to define a range of pivoting of the movable joint portion 41, a stopper pin 49 is provided at the outward flange 47a of the shaft member 47. On the other hand, in the outer barrel member 50, a projection portion 50a oriented toward the outward flange 47a of the shaft member 47 is provided. Then, a range from a rotational position at which one side of the projection portion 50a abuts against the stopper pin 49 to a rotational position at which the other side of the projection portion 50a abuts against the stopper pin 49 is defined as the range of pivoting of the movable joint portion 41.

Note that an O-shaped ring 55 is arbitrarily fitted to each of, e.g., a portion of sliding between the rear grasping portion 22 and the movable joint portion 41, and a part of bonding between the movable joint portion 41 and the bend preventing portion 40 to ensure water tightness of these portions.

Next, a favorable example of grasping for grasping the endoscope 2 configured as described above will be described with reference to FIGS. 7 and 8.

For example, as illustrated in FIG. 7, when, e.g., a surgeon grasps the rear grasping portion 22 in such a manner that the operation portion body 20 (first longitudinal axis O1) is substantially horizontal, the bend preventing portion 40 is oriented in the second direction through a pivoting operation of the movable joint portion 41. Here, in such grasping method, in order to operate, e.g., a treatment instrument from above the hand grasping the rear grasping portion 22, the treatment instrument insertion port 31 is disposed on the outer side in the flexion direction (opposite side of the rear grasping portion 22 with reference to the first longitudinal axis O1) through pivoting of the distal end rotating portion 21.

Then, as a result of the bend preventing portion 40 being directed in the second direction, the universal cable 12 extends downward with the outer side in the flexion direction of the rear grasping portion 22 relative to the operation portion body 20 as a starting point, and a gravity center C of the operation portion 11 is positioned in the vicinity of the second longitudinal axis O2 of the rear grasping portion 22.

Therefore, unnecessary moment acting on the hand grasping the operation portion 11 can be suppressed, and a strain put on, e.g., the wrist can be reduced, enabling achievement of favorable graspability.

In addition, since unnecessary moment acting on the hand grasping the operation portion 11 can be suppressed, it is easy to maintain the operation portion body 20 horizontally. Therefore, in a section from the operation portion 11 to a subject, the insertion portion 10 (flexible tube portion 17) can be prevented from bowing unnecessarily, enabling a bending motion of the bending portion 16 with favorable responsiveness to an operation via the bending operation lever 26. In other words, decrease in responsiveness of bending motion of the bending portion 16 to an operation of the bending operation lever 26 due to generation of, e.g., unintended tension or bowing in the wires inserted in the insertion portion 10 resulting from unnecessary bowing of the insertion portion 10 can be suppressed.

Also, since the insertion portion 10 can be prevented from bowing unnecessarily, followability of torque for the distal end side when an operation to twist the insertion portion 10 can be enhanced and enhancement in durability of the insertion portion 10 can be expected.

Also, since the bend preventing portion 40 extends along the forearm of the hand grasping the rear grasping portion 22, the universal cable 12 can be made to extend with a part that is just in the vicinity of the forearm as a starting point.

Therefore, e.g., when a direction of the operation portion 11 is changed during surgery, handling of the universal cable 12 is easy, enabling provision of more favorable operability. In other words, for example, even if a position of the operation portion 11 is rotated with the first longitudinal axis O1 as a center during, e.g., surgery, the universal cable 12 is less likely to move around. Therefore, the universal cable 12 can be prevented from coming into contact with, e.g., an abdominal region of the surgeon, enabling prevention of a failure due to, e.g., disconnection in the universal cable 12.

On the other hand, for example, as indicated by the alternate long and two short dashes lines in FIG. 7, if the bend preventing portion 40 is oriented in the second longitudinal axis O2 direction with no movable joint portion interposed, a gravity center C' of the operation portion 11 is positioned away from the second longitudinal axis O2. Therefore, unnecessary moment acts on the hand grasping the operation portion 11, and a strain is thus put on, e.g., the wrist. In addition, the generated moment makes it difficult to maintain the operation portion body 20 horizontally, and in the section from the operation portion 11 to the subject, an unnecessary bow is thus more likely to occur in the insertion portion 10, and a bending motion of the bending portion 16 is thus sluggish to an operation of the bending operation lever 26. Furthermore, a bow of the insertion portion 10 increases, for example, the possibility of occurrence of decrease in followability of torque for the distal end side when an operation to twist the insertion portion 10 is performed and/or decrease in durability of the insertion portion 10. Also, since the bend preventing portion 40 is positioned away from the forearm of the hand grasping the rear grasping portion 22, the universal cable 12 extends with a position away from the forearm as a starting point, which makes it difficult to handle the universal cable 12.

Next, for example, as illustrated in FIG. 8, where, e.g., a surgeon grasps the front grasping portion 25 in such a manner that the operation portion body 20 (first longitudinal axis O1) is substantially vertical, the bend preventing portion 40 is oriented in the second direction through a pivoting operation of the movable joint portion 41. In such grasping method, in order to operate, e.g., a treatment instrument from above the hand grasping the front grasping portion 25, the treatment instrument insertion port 31 is disposed on the inner side in the flexion direction (side that is the same as the side on which the rear grasping portion 22 is disposed with respect to the first longitudinal axis O1) through pivoting of the distal end rotating portion 21.

Consequently, the universal cable 12 extends downward from the outer side in the flexion direction of the rear grasping portion 22 via the vicinity of the wrist of the hand grasping the front grasping portion 25, and the gravity center C of the operation portion 11 is positioned in the vicinity of the first longitudinal axis O1 of the front grasping portion 25.

Therefore, unnecessary moment can be prevented from acting on the hand grasping the operation portion 11, enabling reduction of a strain put on, e.g., the wrist and achievement of favorable graspability.

In addition, since unnecessary moment acting on the hand grasping the operation portion 11 can be suppressed, the operation portion body 20 can easily be maintained vertically. Therefore, in the section from the operation portion 11 to a subject, the insertion portion 10 (flexible tube portion 17) can be prevented from bowing unnecessarily, enabling a bending motion of the bending portion 16 with favorable responsiveness to an operation of the bending operation lever 26.

Also, as a result of the universal cable 12 extending through the vicinity of the hand grasping the operation portion 11, for example, even when the direction of the operation portion 11 is changed during, e.g., surgery, handling of the universal cable 12 is easy, enabling more favorable operability. In other word, for example, where the position of the operation portion 11 is rotated with the first longitudinal axis O1 as a center during, e.g., surgery, the universal cable 12 is less likely to move around. Also, since the universal cable 12 extends through the vicinity of the hand grasping the operation portion 11, the universal cable 12 can be prevented from mistakenly coming into contact with the insertion portion 10.

On the other hand, for example, as indicated by the alternate long and two short dashes lines in FIG. 8, if the bend preventing portion 40 is oriented in the second longitudinal axis O2 direction with no movable joint portion interposed, a gravity center C' of the operation portion 11 is positioned away from the first longitudinal axis O1. Therefore, unnecessary moment acts on the hand grasping the operation portion 11, and a strain is thus put on, e.g., the wrist. In addition, the generated moment makes it difficult to maintain the operation portion body 20 vertically, and in the section from the operation portion 11 to the subject, an unnecessary bow is more likely to occur in the insertion portion 10, and a bending motion of the bending operation lever 26 is thus sluggish to an operation of the bending portion 16. Furthermore, a bow of the insertion portion 10 increases, for example, the possibility of occurrence of decrease in followability of torque for the distal end side when an operation to twist the insertion portion 10 is performed and/or decrease in durability of the insertion portion 10. Also, since the universal cable 12 extends via the front side of the operation portion 11, handling of the universal cable 12 is difficult, and furthermore, workability for the treatment instrument insertion port 31 is decreased.

Next, a favorable storage example when the endoscope 2 configured as described above is stored will be described with reference to FIG. 9.

For example, as illustrated in FIG. 9, when the endoscope 2 is stored in a cleaning basin 60 of a cleaning machine, the bend preventing portion 40 is oriented in the first direction through a pivoting operation of the movable joint portion 41. Here, in this case, for example, the treatment instrument insertion port 31 is disposed on the inner side in the flexion direction through pivoting of the distal end rotating portion 21.

Consequently, interference between, e.g., a wall surface of the cleaning basin 60 and the bend preventing portion 40 can be prevented, and the endoscope 2 can be stored in the cleaning basin 60 compactly compared to, e.g., a case where the bend preventing portion 40 is oriented in the second longitudinal axis O2 direction or the second direction (see the alternate long and two short dashes lines in FIG. 9).

According to such embodiment, in the endoscope 2 including the rear grasping portion 22 extending along the second longitudinal axis O2 that is a direction flexed relative to the first longitudinal axis O1 along which the operation portion body 20 extends, the bend preventing portion 40 covering the universal cable 12 extending out from the proximal end side of the rear grasping portion 22 is joined to the proximal end side of the rear grasping portion 22 via the movable joint portion 41 so that the direction of the bend preventing portion 40 can be changed by the movable joint portion 41 to the first direction oriented to the inner side in the flexion direction of the rear grasping portion 22 relative to the operation portion body 20 and the second direction oriented to the outer side in the flexion direction of the rear grasping portion 22 relative to the operation portion body 20, enabling both compact storage and favorable graspability and operability.

Figure 10:
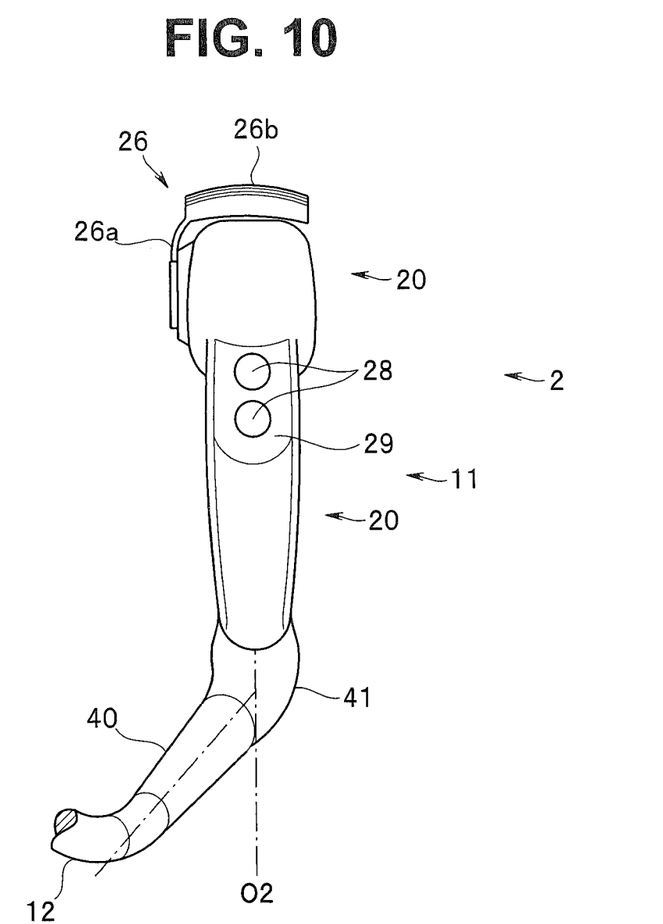
FIG. 10 relates to a first modification and is a back view of an endoscope.

Here, although the above embodiment has been described in terms of an example in which the direction of the bend preventing portion 40 is changed by the movable joint portion 41 to the first direction oriented to the inner side in the flexion direction of the rear grasping portion 22 and the second direction oriented to the outer side in the flexion direction of the rear grasping portion 22, the direction of the bend preventing portion 40 can be change to another direction. For example, as illustrated in FIG. 10, the direction of the bend preventing portion 40 can be changed to a third direction oriented to the outer side in the flexion direction of the rear grasping portion 22 and inclined to a lateral side in the flexion direction. Such change of the direction of the bend preventing portion 40 to the third direction further can effectively suppress interference between the hand and/or the arm of the hand grasping the rear grasping portion 22 and the bend preventing portion 40 and the universal cable 12 in addition to the respective effects described above. Also, where the light source apparatus 3 and/or the video processor 4 are disposed, for example, on a lateral side of a surgeon, the bend preventing portion 40 can be directed toward the light source apparatus 3 and/or the video processor 4. Accordingly, the universal cable 12 can be made to extend with a shortest distance to the light source apparatus 3 and/or the video processor 4. Therefore, it is possible to, when the operation portion 11 is advanced/retracted or twisted during surgery, prevent shortage in length of the universal cable 12 and difficulty in operation due to the shortage.

Figure 11:
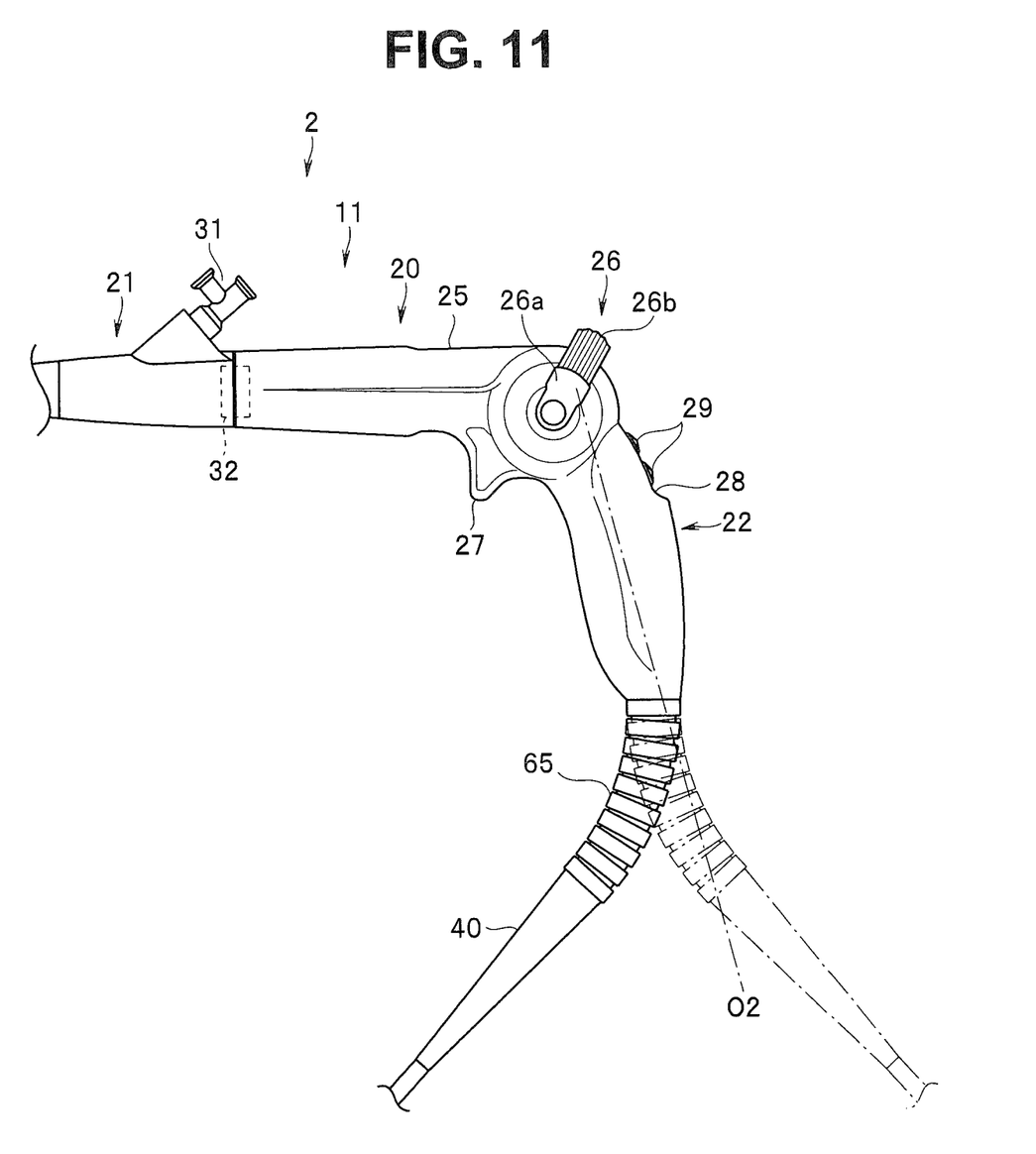
FIG. 11 relates to a second modification and is a side view of an endoscope.

Also, although the above embodiment has been described in terms of an example configuration of the movable joint portion 41 via which the bend preventing portion 40 is pivoted around the pivot axis O3 extending out from the proximal end of the rear grasping portion 22, instead of the movable joint portion 41, for example, as illustrated in FIG. 11, a movable joint portion 65 including a flexible tube such as what is called a gooseneck tube can be employed. Here, for simplicity of description, in the example illustrated in FIG. 11, the movable joint portion 65 is exposed to the outside; however, for ensuring water tightness of the inside of an operation portion 11, the outer side of the movable joint portion 65 is covered by, e.g., a rubber tube.

Figure 12:
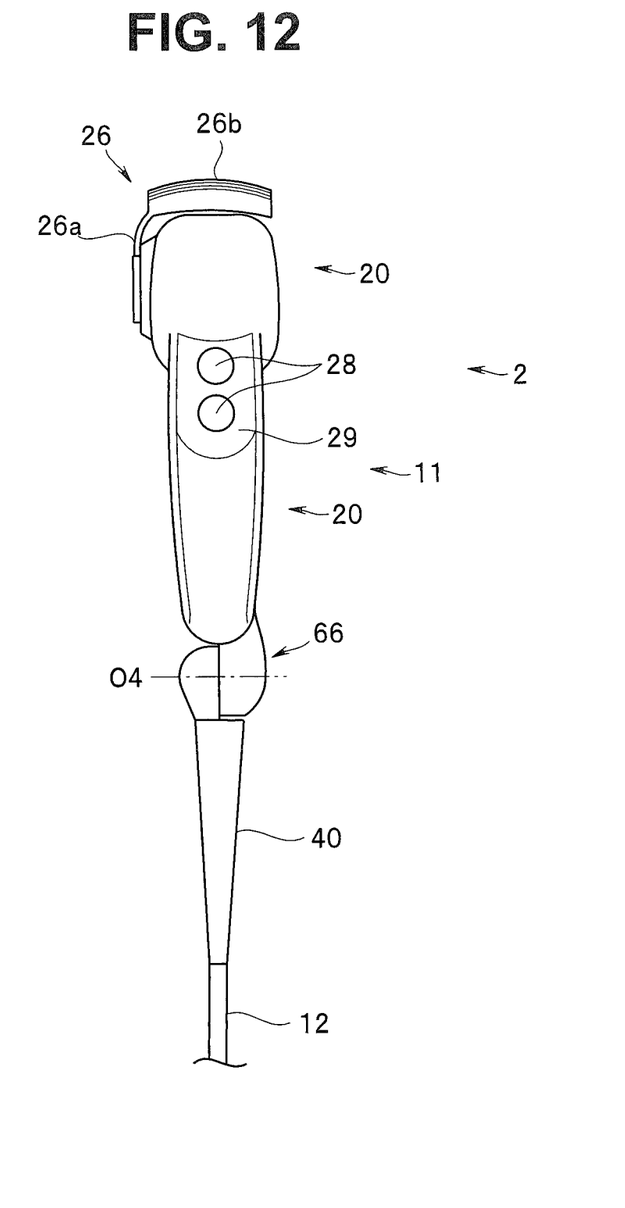
FIG. 12 relates to a third modification and is a back view of an endoscope.
Figure 13:
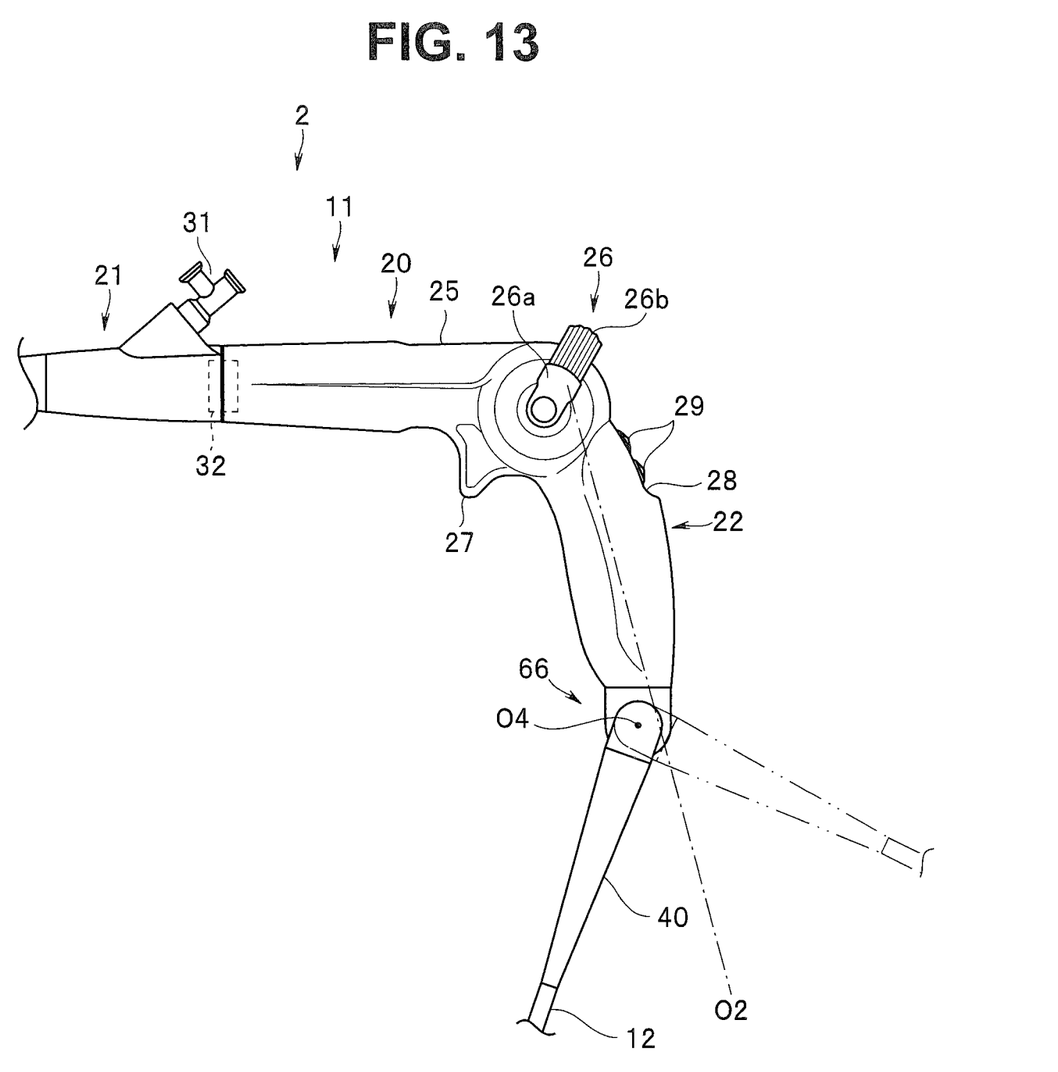
FIG. 13 relates to the third modification and is a side view of the endoscope.

Also, although the above embodiment has been described in terms of an example configuration of the movable joint portion 41 via which the bend preventing portion 40 is pivoted around the pivot axis O3 extending out from the proximal end of the rear grasping portion 22, instead of the movable joint portion 41, for example, as illustrated in FIGS. 12 and 13, a movable joint portion 66 via which a bend preventing portion 40 is pivoted around a pivot axis O4 orthogonal to a second longitudinal axis O2 can be employed.

Note that the present invention is not limited to the embodiment and the respective modifications described above, various modifications and alternations are possible, and such modifications and alternations also fall within the technical scope of the present invention.

What is claimed is:

1. An endoscope comprising:
   an operation body provided so as to be continuous with a proximal end side of an insertion portion, the operation body extending along a first longitudinal axis;
   a rear grasping body provided so as to be continuous with a proximal end side of the operation body, the rear grasping body extending along a second longitudinal axis offset from the first longitudinal axis;
   a cable extending from a proximal end side of the rear grasping body;
   a tube covering the cable on the proximal end side of the rear grasping body; and
   a joint configured to rotatably join the tube to the proximal end side of the rear grasping body so as to rotate the tube relative to the rear grasping body about a pivot axis, the pivot axis being offset from the second longitudinal axis, the pivot axis being offset to a side of the second longitudinal axis that is away from the insertion portion.

2. The endoscope according to claim 1, wherein the joint is configured to change a direction in which the tube extends to a plurality of directions including a first direction in which the tube extends towards the insertion section and a second direction in which the tube extends away from the insertion section.

3. The endoscope according to claim 2, wherein the joint is configured to further change the direction of the tube to extend laterally from the rear grasping body.

4. The endoscope according to claim 2, wherein the first direction is within a range of 20 to 40 degrees, relative to the second longitudinal axis.

5. The endoscope according to claim 2, wherein the second direction is not less than 80 degrees, relative to the second longitudinal axis.

6. The endoscope according to claim 2, wherein the operation body further comprises a front grasping body provided on a distal end side relative to the rear grasping body, the front grasping body being graspable along the first longitudinal axis.

7. The endoscope according to claim 2, wherein the operation body further comprises:
   a distal end rotating body interposed between the insertion portion and the operation body, the distal end rotating body being pivotable around the first longitudinal axis relative to the operation body; and
   a treatment instrument insertion port provided in the distal end rotating body.

* * * * *